United States Patent
Royer

(10) Patent No.: US 6,497,901 B1
(45) Date of Patent: Dec. 24, 2002

(54) RESORBABLE MATRICES FOR DELIVERY OF BIOACTIVE COMPOUNDS

(75) Inventor: Garfield P. Royer, Upperville, VA (US)

(73) Assignee: Royer Biomedical, Inc., Frederick, MD (US)

( * ) Notice: Subject to any disclaimer, the term of this patent is extended or adjusted under 35 U.S.C. 154(b) by 0 days.

(21) Appl. No.: 09/703,710

(22) Filed: Nov. 2, 2000

(51) Int. Cl.⁷ .................... A61K 9/22; A61K 31/70; A61F 2/00; A61F 2/30
(52) U.S. Cl. .................... 424/468; 424/423; 606/77; 514/25
(58) Field of Search .................... 424/423; 606/77; 514/25

(56) References Cited

U.S. PATENT DOCUMENTS

| | | | |
|---|---|---|---|
| 4,946,870 A | 8/1990 | Partain, III et al. | 514/777 |
| 5,200,198 A | * 4/1993 | Geisslinger et al. | 424/489 |
| 5,614,206 A | 3/1997 | Randolph et al. | |
| 6,030,636 A | 2/2000 | Randolph et al. | |

FOREIGN PATENT DOCUMENTS

| | | | |
|---|---|---|---|
| EP | 0 642 785 A2 | 3/1995 | A61K/9/22 |
| WO | WO-9915150 | * 4/1999 | |

* cited by examiner

*Primary Examiner*—Allen J. Robinson
*Assistant Examiner*—Robert M. DeWitty
(74) *Attorney, Agent, or Firm*—Nixon & Vanderhye P.C.

(57) ABSTRACT

This invention relates generally to the production and use of inorganic-conditioning agent complexes for the controlled release of compounds including medicinals. Advantageously, the inorganic used is calcium sulfate and the conditioning agent is calcium stearate.

55 Claims, No Drawings

RESORBABLE MATRICES FOR DELIVERY OF BIOACTIVE COMPOUNDS

FIELD OF THE INVENTION

This invention relates to the general area of drug-delivery systems that are based on resorbable matrices. Sustained and/or controlled release of medicinal agents and other bioactive substances are the primary uses of these systems.

BACKGROUND OF THE INVENTION

Polymer matrices designed for controlled release of bioactive compounds can be non-resorbable or resorbable. In general, resorbable means degradable in the body by erosion from the surface or breakdown from within. The mechanism can involve either a chemical reaction, such as hydrolysis, or dissolution.

Non-resorbable polymers, such as polymethylmethacrylate, have been used for antibiotic delivery. These materials suffer from the disadvantage that they must be retrieved, which involves a second intervention and entails the risk of infection (HW Bucholz, et al., (1970) *Chiburg*, 43, 446).

Resorbable polymer matrices for controlled release are usually based on an oxygenated monomer, which is condensed in organic solvent to yield the polymeric product. The bioactive agent and the polymer are then combined in such a way as to give a timed-release formulation. The combination of active ingredient and polymer often involves organic solvents as well. The use of organic solvents is a decided disadvantage, especially when large-scale production is required. Toxic residues of organic solvents are a concern. Proteins and many polypeptides are incompatible with organic solvents.

The types of polymers in this category include:

polyesters polyanhydrides polyketals poly(orthoesters)

polyurethanes (Burkersroda, F V and Goepferich, A M in *Biomedical Materials*, T Neenan, M Marcolongo and R F Valentini, eds. (1999), page 23, Materials Research Society, Warrendale Pa.).

Naturally occurring proteins may be used as structural components in drug-delivery matrices (Royer, U.S. Pat. No. 4,349,530; Royer, U.S. Pat. No. 5,783,214; Lee, *Science* (1981) 233–235). One deficiency of proteinaceous delivery matrices is that they can exhibit instability especially in environments where an inflammatory reaction is present such as a site of localized sepsis.

WO 99/15150 discloses a stable, yet practical composition for use in inflamed sites comprising an inorganic compound, a matrix polymer and/or a complexing agent. This composition has the advantage of being biocompatible but, unlike synthetic organic polymers, no non-aqueous solvents are required in the preparation. The drug is incorporated as a solid or as part of the matrix polymer solution. The material can also be used as a cement, that is, it can be injected directly into a lesion and allowed to solidify in situ.

OBJECTS OF THE INVENTION

It is an object of this invention to provide a safe resorbable delivery system that can be designed and fashioned to provide controlled release of bioactive substances over a pre-determined time-course.

It is an object of this invention to provide a delivery matrix which when installed as an injectable liquid can solidify in the presence of moisture.

It is an object of this invention to provide a delivery matrix with enhanced stability in acidic and neutral media.

It is an object of the present invention to provide a delivery matrix with improved molecular complexing agents.

SUMMARY OF THE INVENTION

The subject invention relates to a delivery matrix formed by mixing:

a. an inorganic compound capable of undergoing hydration and/or crystallization, plus, b. a conditioning agent which improves stability, extends the residence time, and provides for control of the release profile, and optionally, c. a matrix polymer, and/or d. a complexing agent.

Mixing a bioactive agent with the above components results in a solid composition that is capable of providing sustained release of said agent over a predetermined time period.

DETAILED DESCRIPTION OF THE INVENTION

A. Introduction

The inorganic compound-conditioning agent composites described herein are resorbable by dissolution. No acid is produced as opposed to hydrolytic erosion of polymer matrices such as polyesters.

The inorganic-conditioning agent composite described herein requires no organic solvent in matrix preparation or drug loading. No acid is produced on erosion so it is useful for orthopedic applications. The inclusion of the conditioning agent and advantageously the matrix polymer imparts control over the release profile of the active ingredient and distinguishes this material from unadulterated plaster of Paris which is rigid and safe but is otherwise lacking in performance (D Mackey, et al. (1982) *Clin. Orthop.* 167, 263; G W Bowler, et. al. (1994) J. Trauma, 36, 331). The matrix described in commonly-owned WO 99/15150 may also contain a complexing agent to retard the release of the active ingredient.

The matrix formulation of this invention contains improved hydrophobic complexing agents, e.g., pamoates, and conditioning agents which can serve as water repellants. Water repulsion of these matrices allows for set-up in an aqueous environment. In fact, when a conditioning agent is present, the matrix will solidify when totally submerged. This trait is important when the material is used in orthopedic or dental applications. Examples include filling of periodontal defects or treating an osteomyelitic lesion. Also, the lifetime in the environment, or the body, is extended. This extended residence time is important in the delivery profile. Multiple formulations with different residence times can be combined. The resultant release profile has a desirable form and resembles zero-order. When hydrophobic complexing agents and conditioning agents are used with hydrophobic medicinal agents, the release profiles can be controlled.

Entrapment of bioactive substances within the resorbable biocompatible matrix described herein yields a delivery system, which permits controlled and localized release of a bioactive agent. Inorganic compounds such as $CaSO_4$—1/2

$H_2O$ (calcium sulfate hemihydrate) can be combined with a polymer in the presence of a bioactive agent to produce a solid which constitutes a biocompatible and resorbable delivery matrix (See WO 99/15150—the entire contents of which is incorporated by reference herein). The matrix polymer increases the internal viscosity of the device, which slows the efflux of the bioactive agent.

The production of and advantageous embodiment of the delivery system can be illustrated as follows:

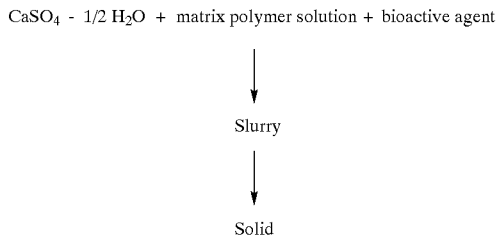

When contacted with water, calcium sulfate hemihydrate is converted to the dihydrate, $CaSO_4$—$2\ H_2O$, which crystallizes. The mass of needle-like crystals produces a porous matrix with high compressive strength, as much as 2000 psi or more. A conditioning agent such as calcium stearate is pre-mixed with the calcium sulfate hemihydrate. The slurry can be injected into the desired location with solidification in situ. This composition is ideal for dental and orthopedic applications. The fact that the slurry can set-up in the presence of moisture is very advantageous.

The delivery matrix is formed by mixing:
  a. an inorganic compound capable of undergoing hydration and/or crystallization, plus
  b. a conditioning agent, and optionally
  c. a matrix polymer, and/or
  d. a complexing agent.

The nature and amount of matrix polymer, the relative proportions of calcium sulfate hemihydrate and liquid, the complexing agent, and the nature and amount of the conditioning agent permit the adjustment of the release profile and residence time of the matrix.

The use of a conditioning agent such as calcium stearate provides improved stability and added control of the release profile and residence time. In addition, it imparts the desirable feature of moisture resistance, which preserves the shape of the mass while setting. When the composition containing calcium stearate is fully submerged after thorough blending, the mass remains intact and setting occurs. This attribute is very important as it allows the installation of the composition into moist areas such as a tooth socket or bone lesion. Water repulsion can also stabilize the solid dosage form with extension of residence time. Calcium stearate is included at a rate of up to 30% w/w, advantageously 2.5–20% ww, based on the amount of inorganic compound, e.g., calcium sulfate hemihydrate. Even higher levels of calcium stearate are obtainable depending on the nature and amounts of other components.

B. Production of Dosage Forms

A delivery matrix of the invention is produced by:
  a. blending of an inorganic such as calcium sulfate hemihydrate and a conditioning agent such as calcium stearate, both in powder form,
  b. mixing with matrix polymer solution (the drug may be dissolved or suspended in the polymer solution),
  c. solidification in a mold or in bulk, and
  d. unmolding or preparing of microbeads by milling and sizing.

The molds made of stainless steel or teflon can be used to prepare cylinders or spheres (e.g., both 3 mm in diameter). The preparation of wafers is also possible. Microbeads can in turn be compressed into tablets with various binding agents to yield another dosage form.

A representative formulation follows:

| Ingredient | Amount |
| --- | --- |
| Calcium sulfate hemihydrate | 0.9 g |
| Matrix polymer solution (10% w/v) | 0.6 ml |
| Calcium stearate | 0.1 g |

When the amount of calcium sulfate hemihydrate is set at about 1 g, the amount of bioactive substance is set in the range of 1–300 mg. The concentration of polymer can be up to 50% (w/v). The conditioning agent is present in the range of 5–30% (w/w) based on calcium sulfate. The ratio of liquid/solid is preferably 0.6.

The calcium sulfate hemihydrate can be sterilized by dry heat (140° for 4 hr); the polymer solution is sterilizable by filtration (0.2-micron filter). Terminal sterilization by gamma irradiation at 15–18 kGy is also effective.

A compilation of useful formulations is shown below in Table 1.

TABLE 1

Useful formulations containing calcium sulfate hemihydrate and the conditioning agent calcium stearate

| Formulation | $CaSO_4$-hh/ CaStearate | Matrix Polymer | Medicinal |
| --- | --- | --- | --- |
| A. | 1 g (95/5) | 0.6 ml (10% PEG, 8,000) | 160 mg amikacin pamoate* |
| B. | 1 g (95/5) | 0.6 ml (10% dextran sulfate) | 200 mg amikacin sulfate |
| C. | 1 g (95/5) | 0.6 ml (10% dextran sulfate) | 200 mg amikacin caprylate* |
| D. | 10 g (95/5) | 6 ml (10% PEG, 8,000) | 2 g cefoperazone |
| E. | 1 g (95/5) | 0.6 ml (20% PEG, 8,000) | 200 mg cefoperazone |
| F. | 1 g (95/5) | 0.6 ml (10% PEG, 8,000) | 160 mg clindamycin pamoate* |
| G. | 1 g (95/5) | 0.6 ml (10% PEG, 8,000) | 260 mg enrofloxacin |
| H. | 1 g (95/5) | 0.6 ml (10% PVP, K-30) | 160 mg silver sulfadiazine |
| I. | 1 g (95/5) | 0.6 ml (10% PEG, 8,000) | 240 mg ofloxacin |
| J. | 1 g (95/5) | 0.6 ml (3% fibrinogen) | 240 mg ofloxacin |
| K. | 1 g (95/5) | 0.6 ml (10% PEG, 8,000) | 100 mg betamethasone |
| L. | 1 g (95/5) | 0.6 ml (10% PEG, 8,000) | 120 mg cis-Pt |
| M. | 1 g (95/5) | 0.6 ml (10% PEG, 8,000) | 120 mg triclosan |
| N. | 1 g (90/10) | 0.6 ml (10% dextran sulfate) | 160 mg muramyl dipeptide |
| O. | 1 g (90/10) | 0.6 ml (10% dextran sulfate) | 160 mg chloroxylenol |
| P. | 1 g (90/10) | 0.6 ml (10% PEG, 8,000) | 160 mg leuprolide acetate |
| Q. | 1 g (90/10) | 0.6 ml (10% PEG, 8,000) | 160 mg bupivacaine pamoate* |
| R. | 1 g (95/5) | — | 160 mg amikacin sulfate |
| S. | 1 g (95/5) | 0.6 ml 10% PS80 | 240 mg amikacin pamoate* |
| T. | 1 g (95/5) | 0.6 ml 10% PEG, 800 | doxycycline HCl |
| U. | 1 g (95/5) | 0.6 ml 10% PS80 | doxycycline pamoate* |
| V. | 1 g (95/5) | 0.6 ml 10% PS80 | clindamycin pamoate* |

*includes complexing agent

1. Inorganic Compounds

Calcium sulfate×$1/2H_2O$ (hemihydrate) (hh) is the preferred inorganic component. The hemihydrate takes up water and crystallizes as the higher hydrate. Unadulterated calcium sulfate matrix exhibits poor drug release profiles.

With conditioning agents, and optionally matrix polymers and complexing agent-active agent complexes the release profiles are improved. Other inorganics can be employed such as calcium silicates, aluminates, hydroxides and/or phosphates (see pages 72, 95, 327 in Reference Book of Inorganic Chemistry (1951) Latimer, W. H., and Hildebrand, J. M., Macmillan, New York, hereby incorporated by reference in its entirety).

2. Conditioning Agents

Conditioning agents are used to slow the erosion rate and permit solidification in the presence of moisture (repels water). All conditioning agents have a hydrophobic moiety. Calcium stearate is an advantageous choice for a conditioning agent that meets the criteria of safety and efficacy. Other calcium salts are useful in this regard. Examples include saturated and unsaturated carboxylic acids, aromatic carboxylic acids, corresponding phosphates, phosphonates, sulfates, sulfonates, and other compounds containing a hydrophobic moiety with a negatively charged anion. Salts of undecylenic acid are useful, in that they provide stability and also antifungal action. The use of calcium as the cation is advantageous but other cations will suffice; the group includes, but is not limited to, zinc, magnesium, aluminum and manganese. The generalized chemical structure can be illustrated as follows:

R—X—M where R is alkyl, alkenyl, alkynyl or aryl, where X is a carboxylate, a carboxylic acid, an aromatic carboxylic acid, a corresponding phosphate, a phosphonate, a sulfate, or a sulfonate, and where M is a metal ion such as calcium, zinc, magnesium, aluminum or manganese.

An example is calcium stearate, $(CH_3[CH_2]_{16}COO^{31})_2Ca^{2+}$

In this case $R=CH_3[CH_2]_{16}$, $X=COO^-$, and M is the metal ion $Ca^+$.

Cationic conditioning agents can also be employed, i.e.,

R—P—Y where R=alky, alkenyl, alkynl or aryl, where P=ammonium, or alkyl ammonium, and where Y=sulfate or phosphate.

3. Matrix Polymers

The preferred matrix polymers for medical use are biocompatible (non-toxic, non-allergenic, non-immunogenic)

water soluble compatible with other components in the formulation

Examples of matrix polymers include chondroitin sulfate, dextran (1–50%) hyaluronic acid (e.g., 1–5%), dextran sulfate, pentosan polysulfate, polyethylene glycol, polyvinylpyrrolidone, proteins such as collagen (gelatin) and fibrinogen and polypeptides. In an advantageous embodiment, a crosslinking agent is added to the matrix polymer. The addition of the crosslinking agent causes a reaction which leads to a higher molecular weight matrix polymer which increases viscosity Diffusion is thereby inhibited. See Royer U.S. Pat. No. 5,783,214 hereby incorporated by reference in its entirety. Counterions, are advantageously sodium or calcium. Chitosan as well as cationic polypeptides, polylysine, and polyarginine are examples of useful polymers that are positively charged at neutral pH.

The function of the matrix polymer is to control the viscosity, which is dependent on the nature, molecular weight and concentration of the polymer. The rationale for using polymers and polymeric complexing agents is based on Stokes law:

$$D\ 1/Mv$$

D=the diffusion coefficient

M=the molecular weight of the medicinal v=the viscosity of the medium

4. Complexing Agents

To the extent that polymeric complexing agents increase the effective molecular weight of the active ingredient, the rate of efflux is slowed according to $D\ 1/Mv$. Complexing agents can be polymers or small molecules. The agents can form ionic bridges or hydrophobic bonds with the molecule to be delivered. The complexes involving the bioactive agents can range from sparingly soluble to soluble. Disodium pamoate is a good example of a complexing agent that forms sparingly soluble adducts with cationic bioactive ingredients. Disodium methylene disalicylate is a similar molecule to disodium pamoate that performs the same function. Procaine and benzathin can be used to reduce the solubility and rate of efflux of anionic bioactive agents. Additional complexing agents are presented in WO 99/15150.

C. Uses of the Compositions of the Invention

Medicinals (both non-protein drugs and medicinal proteins) useful with the matrices of the invention are presented in WO 99/15150. Therapeutics, antigens, adjuvants, and regulatory molecules such as hormones exemplify bioactive agents with medical applications.

The matrix prepared as described above can be combined with soluble bioactive agent and optionally a complexed bioactive agent, to provide an initial burst and intermediate control. As an example clindamycin-HCl free in solution, plus clindamycin-pamoate (as a sparingly soluble salt complex), plus clindamycin-pamoate encapsulated as above in the calcium sulfate-conditioning agent-polymer matrix comprise a three component system for delivery of clindamycin with a desirable release profile. This combination has been employed to provide an antibiotic depot in cats and dogs. Alternatively, a depot can be formed of the soluble drug and the complexed drug alone.

Another embodiment of the invention is a formulation containing a mixture of Drug calcium sulfate, Drug calcium sulfate-calcium stearate 2.5%, Drug calcium sulfate-calcium stearate 5.0% and Drug calcium sulfate-calcium stearate 10%.

Antibiotic formulations can be used to treat localized infections such as osteomyelitis, joint infections, and diabetic foot ulcers. Subsequent to surgical debridement (drainage), beads (e.g., 3 mm), microbeads, or cement is installed at the site of the infection. Infected screw channels in bones can be treated successfully using amikacin cement. Microbeads containing amikacin pamoate are effective in the treatment of joint sepsis. For dead space management following surgical repair of fractures, antibiotic cement can be used.

Another use of antibiotic matrix involves dentistry. Periapical abscesses can be treated with microbeads containing amikacin/clindamycin. Doxycycline cement can be administered by syringe to fill periodontal defects (See Example 16).

Antiparasitics such as ivermectin can be delivered using the delivery system of the invention.

Various anti-infectives useful in conjunction with the formulations of the invention include gentamicin, clarithromycin, doxycycline minocycline and lincomycin, amikacin, penicillin, cefazolin, ciprofloxacin, enrofloxacin, norfloxacin, silver sulfadiazine, imipenem, piperacillin, nafcillin, cephalexin, cefoperazone, vancomycin, tobramycin, nystatin, and amphotericin B or salts thereof (e.g., pamoate salt). Forming the pamoate (a complexing agent) of these anti-infectives to form complexes such as amikacin pamoate, clindamycin and gentamicin pamoate, are useful alone or in the formulations of the invention.

Cis-platin, and other anti-neoplastic agents, can be delivered locally with beads (e.g., 3 mm) or with microbeads prepared as described herein. In one embodiment, localized administration is beneficial in that systemic toxicity is eliminated but concentrations in the area of cancerous tissue are high.

Vaccine antigens can be delivered with the system of the invention, for example, with microbeads (i.m. injection). With only a single injection, a contraceptive antigen (hCG/Dt) elicited long-lived antigenicity (36 weeks) which is sufficiently high to prevent pregnancy. The system of the invention can also be used to deliver DNA and RNA antigens.

The delivery system of the invention can also be used to deliver non-medical bioactive agents include sterilants, pheromones, herbicides, pesticides, insecticides, fungicides, algicides, growth regulators, antiparasitics, repellents, and nutrients. (See also WO 99/15150).

D. Production of the Matrix and Modes of Administration

Administration of the solid matrix can be by surgical implant, oral, i.p., i.a. or p.a. The liquid injection can be s.c., i.m, or i.p. Advantageously, the administration is done by parenteral injection.

a. Cement 1 g of calcium sulfate/calcium stearate (1–25% w/w) plus amikacin pamoate (100–320 mg) are thoroughly mixed and contacted with 0.6 ml of aqueous dextran sulfate (10% w/v). After blending to a smooth slurry (30s), the material is transferred to a 5 ml syringe and installed in vivo where it solidifies. Amikacin sulfate can be blended with amikacin pamoate to adjust the release profile. Presence of the calcium stearate allows for the solidification in the presence of moisture.

b. Beads/Cylinders

Sterile 3 mm beads can be installed individually with mosquito forceps or in groups using a cannula. A teat cannula is a safe tool for installation of beads and cylinders. This approach has been successfully used in the treatment of squamous cell carcinoma via intralesional chemotherapy with 3 mm beads of the invention containing cis-Pt (7%).

c. Microbeads

Injection

Sterile microbeads (45–150 microns) (dry) are suspended in a suitable liquid for injection just prior to use. When antibiotics are involved, a solution of the antibiotic of choice may be used as the suspending liquid. For example, in treating a septic joint, amikacin solution (3 mil/25%) is used to suspend microbeads (300 mg) containing amikacin pamoate prepared as described in Example 4. An "initial burst" provided by the soluble amikacin sulfate is followed by the amikacin that elutes from the microbeads. A similar approach is appropriate for creating a subcutaneous depot of antibiotics and other active ingredients.

Oral

Microbeads are mixed with food or feed. The composition of the invention is tasteless and in some cases will mask the taste of a bioactive compound. In addition, the microbeads of the invention can be included in a capsule for oral delivery.

The following Examples are illustrative, but not limiting of the compositions and methods of the present invention. Other suitable modifications and adaptations of a variety of conditions and parameters normally encountered which are obvious to those skilled in the art are within the spirit and scope of this invention.

EXAMPLES

Example 1

Synthesis of Amikacin Pamoate

Disodium pamoate (865 mg) was dissolved in a minimum amount of water. Amikacin sulfate (782 mg), dissolved in a minimum amount of water, was added to the sodium pamoate solution and mixed thoroughly at room temperature. The precipitate was collected by filtration and washed with two portions (5 ml) of cold water. The material was dried in a vacuum dessicator for 48 hrs.

Yield: 70%. MP: 235–244° with decomposition.

Example 2

Synthesis of Clindamycin Pamoate

Disodium Pamoate (216 mg) was dissolved in a minimum amount of water. Clindamycin-HCl (461 mg), dissolved in a minimum amount of water, was added to the sodium pamoate solution and mixed thoroughly at room temperature. The precipitate was collected by filtration and washed with two portions (5 ml) of cold water. The material was dried in a vacuum dessicator for 48 hrs.

Yield: 78%. MP: 189–194°.

Example 3

Preparation of Calcium Sulfate/calcium Stearate Formulation Containing Enrofloxacin Calcium sulfate and calcium stearate powders were thoroughly mixed in a weight ratio of 19/1. This mixture (1 g) was then blended with finely ground enrofloxacin (160 mg). To this solid mixture was added 0.6 ml of polyethyleneglycol solution (PEG-MW 8,000, 10% w/v). The slurry was mixed for one minute and then allowed to solidify in bulk or was injected into a teflon mold for the production of 3 mm beads.

Example 4

Formulation Containing Amikacin Pamoate

To calcium sulfate (1 g) was added 0.16 g of amikacin pamoate which had been finely ground. The powders were thoroughly mixed and contacted with 0.6 ml of PEG-8000 (10% w/v). After mixing for about 1 min, the slurry was injected into a mold or allowed to solidify in bulk. An identical procedure is used with calcium sulfate hemihydrate containing 5% calcium stearate. Another variation which produces a convenient preparation is to add 10% (w/v) of polysorb 80 to the 10% PEG-8000.

Example 5

Formulation of Clindamycin Pamoate

This procedure was identical to Example 3 except that clindamycin pamoate (160 mg) was substituted for enrofloxacin.

Example 6

Formulation of Cefoperazone

Calcium sulfate and calcium stearate powders were thoroughly mixed in a weight ratio of 19/1. This mixture (0.8 g) was then blended with finely ground cefoperazone (200 mg). To this solid mixture was added 0.6 ml of polyethyleneglycol solution (PEG-MW 8,000, 10% w/v). The slurry was mixed for one minute and then allowed to solidify in bulk or was injected into a teflon mold for the production of 3 mm beads.

Example 7

In Vitro Release Profiles (3 mm Beads)

Four 3 mm beads were incubated in 400 μl of PBS, pH 7.4 at 37° C. The PBS buffer was changed at 24-hour intervals over a 4-day period and the samples were analyzed for eluted drug either spectrophotometrically or by microbiological assay. Representative results are shown below.

| Day | % Released |
|---|---|
| A. Amikacin pamoate | |
| 1 | 33 |
| 2 | 14 |
| 3 | 3.3 |
| 4 | 2.9 |
| B. Clindamycin pamoate | |
| 1 | 5.7 |
| 2 | 5.7 |
| 3 | 5.7 |
| 4 | 5.7 |
| C. Enrofloxacin | |
| 1 | 2.4 |
| 2 | 2.4 |
| 3 | 2.4 |
| 4 | 1.9 |
| D. Cefoperazone | |
| 1 | 11 |
| 2 | 10 |
| 3 | 6 |
| 4 | 6 |

Example 8

In Vitro Release Profile with Microbeads (45–150 Microns)

Cefoperazone microbeads were prepared as described in Example 6 (solidification in bulk). Milling and sieving the solid matrix produced the microbeads. Microbeads (100 mg) were incubated in 400 μl of PBS, pH 7.4 at 37° C. The PBS buffer was changed at 24-hour intervals over a 4-day period and the samples were analyzed for eluted drug either spectrophotometrically or by microbiological assay. Results are shown below.

A. Release of antibiotic from Cefoperazone microbeads.

| Day | % Released |
|---|---|
| 1 | 15 |
| 2 | 11 |
| 3 | 11 |
| 4 | 16 |

B. Release of antibiotic Enrofloxacin microbeads (10% enrofloxacin, 5% calcium stearate, 10% PEG).

| Day | % Released |
|---|---|
| 1 | 1.9 |
| 2 | 1.3 |
| 3 | 1.9 |
| 4 | 1.5 |

Example 9

Formulation of Ivermectin

Ivermectin (Ivermectin M. I., $12^{th}$ Edition, p. 5266, #5264) (110 mg) was finely ground and combined with calcium sulfate hemihydrate (890 mg) which contained 5% calcium stearate w/w. After thorough mixing, 0.6 ml of polyethyleneglycol solution (PEG-MW 8,000, 10% w/v) was added. After solidification, the product was allowed to stand for 24 hr, milled and sized (45–150 microns). The material was used to successfully deworm horses at a dosage of 200 mcg/kg, a.i.

The table below shows treatment of parasites in naturally infected horses—eggs per gram of feces as a function of time. EPG was determined at day 5, day 7, and day 14. Five animals were included in each group.

| Subject Group (5 animals) | Mean EPG | | |
|---|---|---|---|
| | day-5 | day 7 | day 14 |
| Untreated Controls | 230 | 334 | 246 |
| Positive Controls-Eqvalan ® | 320 | <1 | <1 |
| Formulation of-Ivermectin | 262 | <1 | <1 |

Example 10

Use of Formulation of Amikacin Pamoate Microbeads to Treat an Equine Joint Infection Five-year-old, TB gelding presented with a septic left rear hock joint, which resulted from a puncture wound. Lameness was grade 5—non-weight-bearing. Prior therapy included systemic treatment with penicillin and gentamicin without effect. The joint fluid showed elevated protein and WBC. Culture revealed S. Aureus. Following joint lavage, a suspension containing 300 mg of amikacin pamoate microbeads was injected through an 18-gauge needle. The horse showed rapid improvement and the joint fluid was found to be sterile at day three. At five days post treatment, the horse was sound.

Example 11

Treatment of Osteomyelitis Using Formulation of Amikacin Pamoate

A one-year old Connemara filly presented with osteomyelitis/joint sepsis in the right hind coffin joint. Three days of systemic treatment with ampicillin plus gentamycin produced no improvement. Following debridement, Ig of formulation (5% calcium stearate, described in Example 4) was injected in the lesion following lavage with lactated Ringer's solution. For injection the cement was loaded into a five-ml syringe after 30 s of mixing time.

Heat and swelling receded after two days. The horse was sound ten days post-treatment. Three months post-treatment, owners said the horse was 100% sound.

Example 12

Treatment of Osteomyelitis and Septic Tendon Sheath

A three-year-old Arab filly presented with osteomyelitis of the talus with an accompanying septic tendon sheath. Prior treatment consisted of i.m. injections of penicillin for 5 days with no result. The osteomyelitic lesion was curetted; the tendon sheath was debrided and flushed. Five holes (3.2 mm×4 mm deep) were drilled in the talus. The holes were filled with the formulation of amikacin pamoate as described in Example 11. Effusion diminished and the horse became completely sound. Follow-up at 3 months and 11 months revealed that the horse successfully returned to intended use.

Example 13

Antibiotic Depot/formulation of Clindamycin Pamoate Plus Unformulated Clindamycin pamoate

Treatment of an Upper Respiratory Infection

A mixed-breed dog (20 lb, age 5) was treated for a chronic respiratory infection with clindamycin pamoate. The formulation of clindamycin-pamoate was co-administered with unformulated clindamycin pamoate to provide a long-lasting depot. Finely ground clindamycin pamoate (100 mg) was mixed with the formulation of clindamycin pamoate (1.7 g, Example 5). The mixture was suspended in sterile water and injected, s.c., in two portions on either side of the neck. The animal was asymptotic after four days.

Example 14

Treatment of an Infected Bite with Clindamycin Pamoate

An English foxhound pup (10 lb) suffered from an infected bite on the right forelimb. Culture revealed a mixed infection with anaerobes. Unformulated clindamycin pamoate (150 mg) was suspended in sterile water and injected, s.c., in the scruff of the neck. The hound's temperature returned to normal on the third day post treatment. After 6 days without further treatment the hound's leg showed very little swelling and the lameness disappeared.

Example 15

Synthesis of Doxycycline Pamoate

Disodium Pamoate (54 mg) was dissolved in a minimum amount of water. Doxycycline-HCl (120 mg), dissolved in minimum amount of water, was added to the sodium pamoate solution and mixed thoroughly at room temperature. The precipitate was collected by filtration and washed with two portions (5 ml) of cold water. The material was dried in a vacuum dessicator for 48 hors.

Yield: 85%. MP: 190–196°.

Example 16

Formulation Containing Doxycycline Pamoate

To calcium sulfate (1 g) was added 0.16 g of doxycycline pamoate which had been finely ground. The powders were thoroughly mixed and contacted with 0.6 ml of PEG-8000 (10% w/v). After mixing for about 1 min, the slurry was injected into a mold or allowed to solidify in bulk. An identical procedure is used with calcium sulfate hemihydrate containing 5% calcium stearate. Another variation which produces a convenient preparation is to add 10% (w/v) of Polysorb 80 to the 10% PEG-8000. As a cement, this formulation is useful in treating periodontal defects. In this case, the slurry is transferred to the barrel of a 5 ml syringe and installed through a 14 gauge needle with a blunt end.

Example 17

Formulation with Thrombin/fibrinogen

Fibrinogen can be used as the matrix polymer when thrombin is included in the formulation-thrombin converts fibrinogen to fibrin which polymerizes. The amount of thrombin and fibrinogen can be adjusted to provide a gelation time that is longer than the setting time of the inorganic matrix. This sequence results in a matrix within a matrix.

Thrombin (1 mg) is mixed with 4.7 g of calcium sulfate/calcium stearate (19/1) to yield a stock (solid) solution. This solid is then diluted, as appropriate, to give 0.1 units of thrombin/gram of calcium sulfate/calcium stearate.

Erythropoietin (4.5 mg) is mixed with 1 g of calcium sulfate/calcium stearate/thrombin (0.1 units). To this solid is added 300 ul of a solution containing fibrinogen (6%) and serum albumin (5%). The fibrinogen/serum albumin solution is made with Hepes buffer (0.03M, pH 7.2). After 48 hrs the hard solid is milled and sized to 45–150 microns.

Similar preparations can be made with other bioactive polypeptide hormones, antigens, antibiotics, and other bioactive compounds.

Example 18

Formulations with Cross-linked Albumin (Gelatin)

One g of calcium sulfate/calcium stearate (19/1) is mixed with 160 mg of finely ground enrofloxacin. To this solid is added 300 ul of 3% serum albumin and 300 ul of glutaraldehyde solution (0.25%). Mixing for 30 s yields a smooth slurry which is poured into a tray; the material is allowed to dry for 48 hrs at room temperature. The hard solid is milled and sized to the range of 45–150 microns. A 3% solution of gelatin can be substituted for the serum albumin solution. Other useful matrix polymers include chitosan, bis-amino-PEG, polypeptides containing lysine, and other biocompatible polymers which contain electrophilic functional groups. Use of cross-linked matrix polymer is especially appropriate for preparing formulations for the long-term, continuous delivery of antigens.

It will be readily apparent to those skilled in the art that numerous modifications and additions may be made to both the present invention, the disclosed device, and the related system without departing from the invention disclosed.

What is claimed is:

1. A matrix delivery system comprising:
   a) calcium sulfate, and
   b) a conditioning agent, wherein
      said calcium sulfate of said matrix delivery system becomes a solid by hydration, and wherein
      said conditioning agent is present in the range of 5–30% (w/w). based on calcium sulfate.

2. A system as in claim 1, further comprising an antiparasitic.

3. A system as in claim 1, further comprising a matrix polymer.

4. A system as in claim 3, wherein the matrix polymer is a biopolymer selected from the group consisting of hyaluronic acid, chondroitin sulfate, dextran, dextran sulfate, polyethylene glycol and protein.

5. A system as in claim 1, wherein said conditioning agent is selected from the group consisting of calcium stearate, zinc undecylenate, magnesium palmitate, sodium laurate, calcium napthenate, calcium oleate, lauryl ammonium sulfate.

6. A system as in claim 1, wherein said conditioning agent is calcium stearate.

7. A system as in claim 1, further comprising a complexing agent selected from the group consisting of chondroitin sulfate, polyglutamic acid, polyaspartic acid, pamoic acid, polynucleotides, a cationic polypeptide, cyclodextrin, polyoxyethylene alcohol, ester or ether, and defatted albumin.

8. A system as in claim 7, wherein said polyoxyethylene alcohol, ester or ether is a surfactant.

9. A system as in claim 7, wherein said cyclodextrin is hydroxypropyl beta cyclodextrin.

10. A system as in claim 7, wherein said complexing agent is a lipid or a liposome.

11. A system as in claim 10, wherein said lipid is a lipid of biological origin selected from the group consisting of cholesterol and lecithin.

12. A system as in claim 2, comprising calcium sulfate, calcium stearate, and a glycosaminoglycan.

13. A system as in claim 12, wherein said glycosaminoglycan is hyaluronic acid or chondroitin sulfate.

14. A system as in claim 1, wherein said system is in the form of a bead, a wafer, a tablet, a sphere, a granule or a cylinder.

15. A system as in claim 1, wherein said conditioning agent contains a hydrophobic moiety.

16. A system as in claim 1, comprising calcium sulfate, calcium stearate and hyaluronic acid.

17. A system as in claim 1, further comprising a medicinal.

18. A system as in claim 17, wherein said medicinal is a salt.

19. A composition comprising a system as in claim 17, and a soluble medicinal.

20. A composition comprising a system as in claim 17, and a medicinal and a complexing agent.

21. A composition as in claim 19, comprising
   a) a matrix containing calcium sulfate, calcium stearate, amikacin, and
   b) amikacin sulfate.

22. A composition as in claim 20 comprising:
   a) a matrix containing calcium sulfate, calcium stearate, amikacin, and
   b) amakacin pamoate.

23. A composition as in claim 21, further comprising amikacin sulfate.

24. A system as in claim 17, wherein said medicinal is a drug precursor.

25. A system as in claim 17, wherein said medicinal is a protein medicinal.

26. A system as in claim 17, wherein said medicinal is an anti-infective selected from the group consisting of gentamicin, clarithromycin, doxycycline, minocycline and lincomycin, amikacin, penicillin, cefazolin, ciprofloxacin, enrofloxacin, norfloxacin, silver sulfadiazine, imipenem, piperacillin, nafcillin, cephalexin, cefoperazone, vancomycin, tobramycin, nystatin, silver sulfadiazine, imipenem, and amphotericin B or salts thereof.

27. A system as in claim 17, wherein said medicinal is an antibiotic.

28. A system as in claim 17, wherein said medicinal is an antineoplastic agent.

29. A system as in claim 17, wherein said medicinal is an anesthetic.

30. A system as in claim 29, wherein said anesthetic is lidocaine.

31. A system as in claim 30, wherein the lidocaine is selected from the group consisting of lidocaine hydrochloride and lidocaine pamoate.

32. A system as in claim 1, further comprising a non-medicinal compound.

33. A system as in claim 32, wherein said non-medicinal compound is selected from the group consisting of a sterilant, a pheromone, a herbicide, a pesticide, an insecticide, a fungicide, an algicide, a growth regulator, a nematicide, a repellent, and a nutrient.

34. A system as in claim 33, further comprising a herbicide.

35. A system as in claim 32, wherein said matrix polymer is selected from the group consisting of polyethyleneglycol, polyvinylpyrrolidone, polyvinylalcohol, starch, xanthan, cellulose and a cellulose derivative.

36. A system as in claim 32, wherein said complexing agent is a complexing agent selected from the group consisting of a polyoxyethylene ester or ether, and a surfactant of either biological or non-biological origin.

37. A system as in claim 32, wherein said complexing agent is selected from the group consisting of polyacrylic acid, alginic acid, dextran sulfate, polyvinylpyridine, chitosan, polyvinylamine, polyethyleneimine and a lipid.

38. A system as in claim 1, wherein said system is porous.

39. A system as in claim 3, wherein said matrix polymer is dextran sulfate.

40. A system as in claim 3, wherein said matrix polymer is polyethyleneglycol.

41. A system as in claim 39, further comprising amikacin.

42. A system as in claim 39, further comprising silver sulfadiazine.

43. A composition comprising amikacin sulfate and amikacin pamoate.

44. A method of producing sustained release of a medicinal in a mammal comprising administering the system of claim 1 and a medicinal to said mammal.

45. A method as in claim 44, wherein said administration is by subcutaneous injection.

46. A method of treating infection in a mammal comprising administering a composition comprising the system of claim 1 and an anti-infective to said mammal.

47. A method as in claim 46, wherein said anti-infective is selected from the group consisting of gentamicin, clarithromycin, doxycycline minocycline and lincomycin, amikacin, penicillin, cefazolin, ciprofloxacin, enrofloxacin, tobramycin, norfloxacin, silver sulfadiazine, imipenem, piperacillin, nafcillin, cephalexin, vancomycin, nystatin, and amphotericin B or salts thereof.

48. A method of producing a delivery system comprising mixing (a) calcium sulfate, (b) a matrix biopolymer, and (c) a conditioning agent, wherein said conditioning agent is present in the range of 5–30% (w/w) based on calcium sulfate.

49. A method as in claim 48, wherein said inorganic compound, and conditioning agent are premixed and then added to said matrix biopolymer.

50. A method of scaffolding bone or filling a defect in bone comprising administering to said bone the delivery system of claim 1.

51. A method as in claim 50, wherein said delivery system further comprises freeze-dried bone.

52. A method for administering a delivery system comprising:
(a) mixing calcium sulfate, a conditioning agent in the range of 5–30% (w/w) based on calcium sulfate, and a medicinal to form a slurry;
b) administering said slurry to said mammal, wherein said slurry solidifies after administration.

53. An antibiotic selected from the group consisting of amikacin pamoate, clindamycin pamoate and gentamicin pamoate.

54. A method of producing a delivery system comprising mixing:
a) an inorganic compound capable of undergoing hydration and/or crystallization, a conditioning agent and thrombin,
b) fibrinogen,
wherein mixing (a) and (b) converts fibrinogen to fibrin.

55. A system as in claim 2, wherein said antiparasitic is ivermectin.

* * * * *